United States Patent
Lakaye et al.

(10) Patent No.: US 11,737,461 B2
(45) Date of Patent: Aug. 29, 2023

(54) CITRATE PERHYDRATES AND USES THEREOF

(71) Applicant: BIOREM ENGINEERING SA, Martigny (CH)

(72) Inventors: Frederic Lakaye, Ovronnaz (CH); Alain Gaume, Romont (CH); Katia Gindro, Romanel-sur-Morges (CH); Sylvain Schnee, Thoiry (FR); Wendy Hardy, Geer (BE); Marc Noël, Chaumont-Gistoux (BE); Maurice Semer, Modave (BE)

(73) Assignee: BIOREM ENGINEERING SA, Martigny (CH)

( * ) Notice: Subject to any disclaimer, the term of this patent is extended or adjusted under 35 U.S.C. 154(b) by 0 days.

(21) Appl. No.: 17/264,286

(22) PCT Filed: Aug. 2, 2019

(86) PCT No.: PCT/EP2019/070941
§ 371 (c)(1),
(2) Date: Jan. 28, 2021

(87) PCT Pub. No.: WO2020/025816
PCT Pub. Date: Feb. 6, 2020

(65) Prior Publication Data
US 2021/0298301 A1  Sep. 30, 2021

(30) Foreign Application Priority Data

Aug. 3, 2018  (FR) ...................................... 1857317

(51) Int. Cl.
*A01N 37/36* (2006.01)
*A01N 25/12* (2006.01)

(52) U.S. Cl.
CPC ............. *A01N 37/36* (2013.01); *A01N 25/12* (2013.01)

(58) Field of Classification Search
CPC ................................ A01N 37/36; A01N 25/12
See application file for complete search history.

(56) References Cited

U.S. PATENT DOCUMENTS 3,647,869 A * 3/1972 Kaloff ...................... A61Q 5/08
510/318
4,655,975 A  4/1987 Snoble

FOREIGN PATENT DOCUMENTS

FR  2219150 A1  9/1974
WO  WO-9528840 A1 * 11/1995 ............. A01N 59/00

* cited by examiner

*Primary Examiner* — Snigdha Maewall
(74) *Attorney, Agent, or Firm* — Arrigo, Lee, Guttman & Mouta-Bellum LLP

(57) ABSTRACT

The invention relates to citrate perhydrates and to the uses of citrate perhydrates, in particular as biocides, in particular pesticides, more particularly phytopharmaceuticals.

21 Claims, 6 Drawing Sheets

A

B

Figure 1:
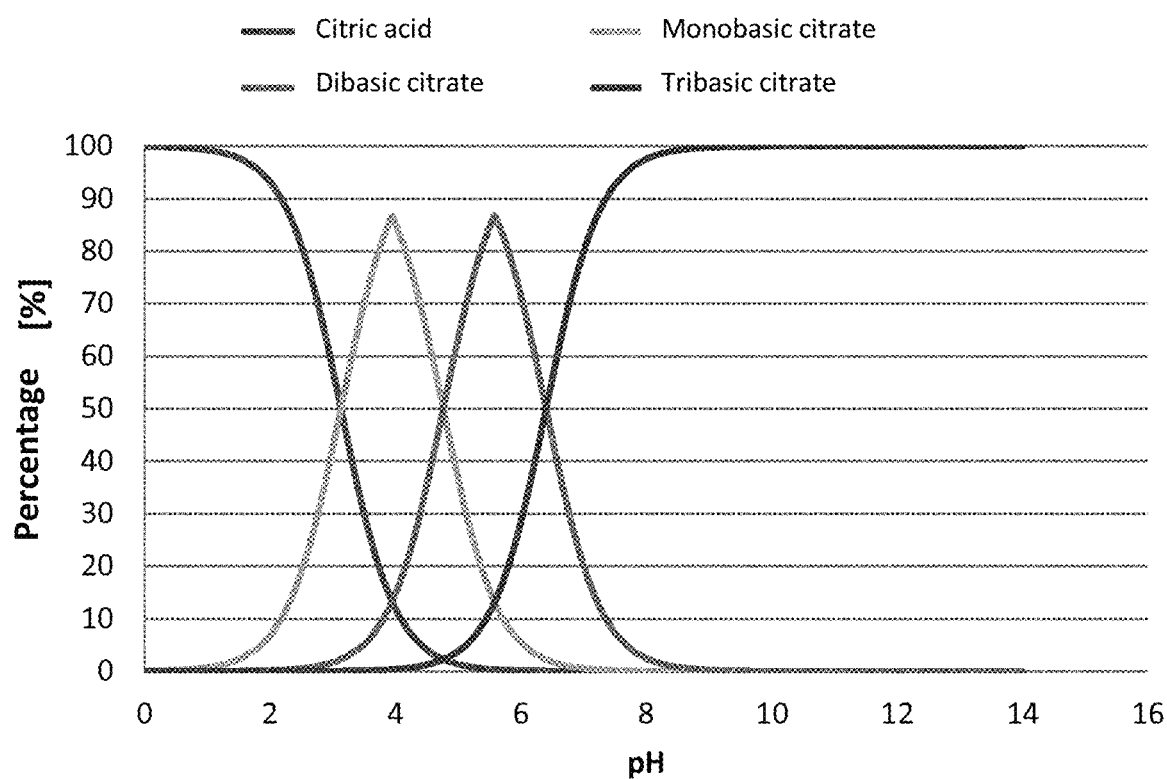

FIGURE 8
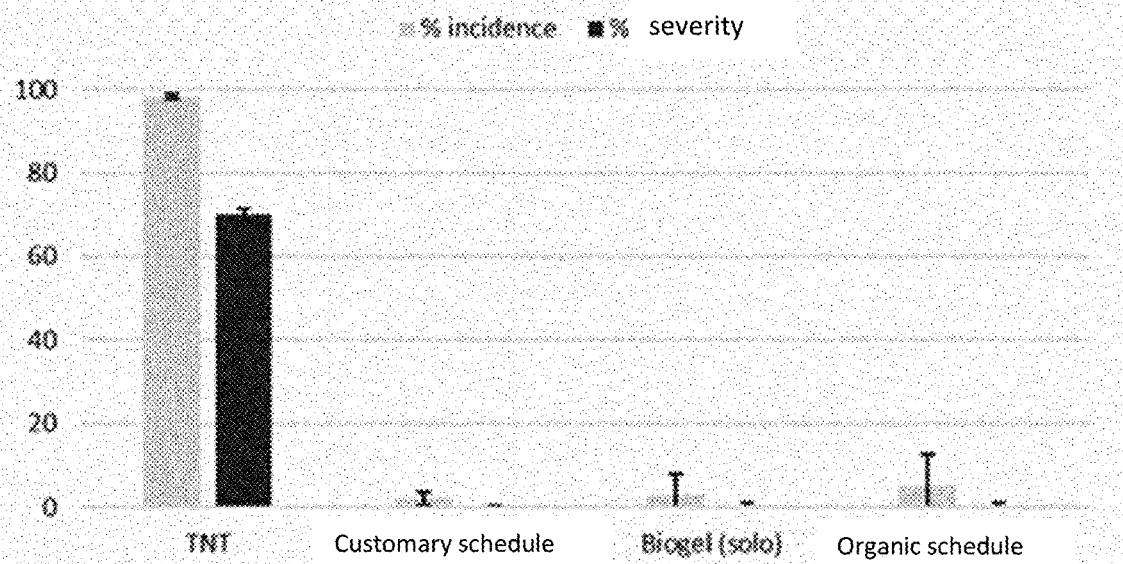
Figure 8A
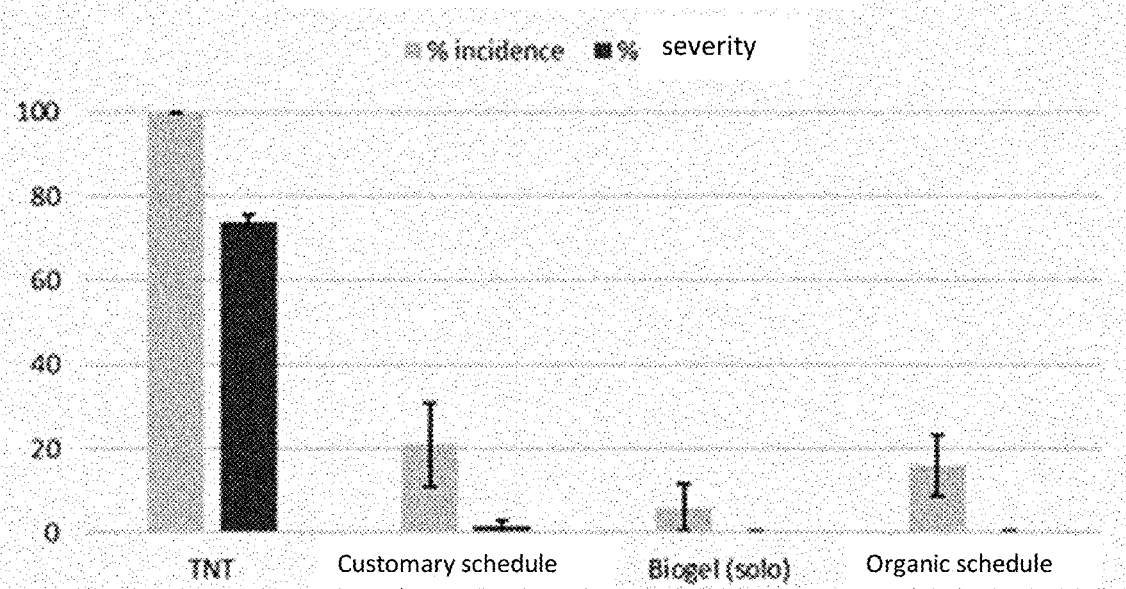
Figure 8B

CITRATE PERHYDRATES AND USES THEREOF

The invention relates to citrate perhydrates and also to uses of citrate perhydrates, in particular as biocides, in particular pesticides, more particularly phytopharmaceuticals.

The invention also relates to a method for preparing these novel biobased organic molecules, which are in the form of a soluble, stable crystalline powder and which contain, at physiological pH, a novel solid form of hydrogen peroxide.

Biocides denote a large family of chemical substances bringing together pesticides, in particular phytopharmaceutical products, and antimicrobial agents for medical, veterinary, domestic or industrial use, as well as disinfectants for fluids and surfaces, in particular for water, air, floors, swimming pools, work surfaces, toilets, etc.

Antimicrobial agents and disinfectants are able to reduce as far as possible the risk of infection for humans or animals. Since some bacteria, moulds, yeasts and viruses may lead to serious illnesses, disinfection is an essential part of everyday life, in particular in the medical sector and in homes. The importance of disinfection for human well-being is often underestimated. Over the course of the previous centuries, more people died following large-scale epidemics (plague, cholera, smallpox or flu) than during wars. Until the start of the 20th century, bacterial infections were often fatal, even in industrialized countries. In less fortunate countries, infectious diseases, which mainly originate from inadequate hygiene, are nowadays still the cause of numerous deaths. There is therefore a strong demand for antimicrobial agents and disinfectants which are effective and inexpensive, in particular in the medical sector.

This demand also exists in the agricultural sector for pesticides, in particular for fungicidal substances. Indeed, pesticides such as fungicides, insecticides and herbicides are important auxiliary agents for agriculture, in order to protect and increase crop yields. Agricultural workers aim to optimise production by enhancing conditions for growth while minimising attacks by pests against seeds, seedlings, plants and fruit. Such pests include bacteria, fungi, etc. Considerable attention has been given to antimicrobial compounds which attack bacteria and fungi on seeds, seedlings, growing plants and fruit. The use of fungicides in agriculture is made necessary by the losses caused by a wide variety of microorganisms which are pathogenic to plants. To be economical, the costs of combatting plant diseases by applying bactericides and fungicides must be offset by much greater potential gains. Significant tonnages of fungicides are required in the farming of apples, pears, bananas, cereals, cacao, coffee, cotton, potatoes, tobacco, eating grapes and wine grapes, and other common fruit and vegetables such as celery, leeks, onions, lettuce, potatoes, garlic, shallots, peppers, beans, tomatoes, almonds, peanuts and many more.

In particular, according to figures from 2016, the global market for plant-protection fungicides is estimated at more than 9.7 billion euros, in particular 3.9 billion Euros in Europe and 3.6 billion Euros in America.

Within this market, there is a strong demand for fungicides in the wine sector. For example, in France, the total consumption of fungicidal products for treating vines is estimated at €400 million for a total surface area of 792,000.00 hectares.

Customary biocides are often toxic, carcinogenic, mutagenic, teratogenic, expensive and/or ineffective. Moreover, in order to obtain a powerful disinfectant effect, highly persistent chemical substances were used in the past as disinfectants in order to obtain effective and long-lasting protection against microorganisms. However, this persistence leads to considerable environmental problems. This is because highly persistent biocides accumulate in underground water and/or in the food chain and lead to major ecological and health problems. For example, ecological problems may arise when high concentrations of biocides reach biological water treatment plants. In the event of high concentrations of biocides, the growth of the microorganisms needed by these plants is affected, which may lead to partial or total failure of the waste water treatment facility. Moreover, persistent composites may accumulate in the sewage sludge.

In order to overcome the health-related and ecological disadvantages of these customary persistent biocides, the use of less dangerous substances was envisaged in the past, in particular the use of natural substances liable to have disinfectant properties. However, their improved environmental compatibility was obtained to the detriment of their efficacy and their ability to protect against microorganisms. Due to this disadvantage, less importance has been attached to these ecologically friendly disinfectants and the use of environmentally dangerous compounds predominates.

Peracetic acid is a powerful oxidising agent known to have virucidal, bactericidal, fungicidal and algicidal properties. Peracetic acid was patented in the 1950s for the treatment of plant tissues, in particular intended to be processed, in particular for the treatment of fruit and vegetables, in order to reduce the deterioration thereof by bacteria and fungi (U.S. Pat. No. 2,522,640). Nowadays, peracetic acid is commonly used during the processing and handling of food as a disinfectant for surfaces in contact with the food, but also for fruit, vegetables, meat and eggs. In the production of fruit and vegetables, aqueous peracetic solutions have been suggested for controlling pathogenic organisms on growing plants. However, one of the major problems associated with liquid aqueous solutions of peracetic acid is that these solutions are corrosive, highly acidic, highly reactive, and strongly odorising, which makes them difficult and dangerous to use both for users and for the treated plants.

Novel biobased zero-residue compounds of citrate perhydrate type have now been developed, which form the subject matter of the present application and which make it possible to release active agents, namely hydrogen peroxide and also citrates, which can act synergistically, and which have equivalent efficacy to benchmark biocides while being categorised as GRAS (Generally Recognized As Safe) by the Food and Drug Administration. Indeed, the degradation products of the citrate perhydrates of the invention are food additives such as sodium citrates (E331), potassium citrates, zinc citrates, etc.

Moreover, the compounds of the invention may be in powder form, which can easily be synthesised according to an economical process, packaged, transported and handled. These powders are physically and chemically stable, i.e. there is no significant alteration over time (for example after one year at ambient temperature, i.e. at a temperature of from 20 to 25° C.), in their physical state and in their chemical composition, in particular in their concentration of active oxygen. In addition, they are odourless, highly water soluble, and the corresponding aqueous solutions have a broad range of possible pH of between 4 and 8. Indeed, the pH obtained by dissolving other compounds containing hydrogen peroxide (for example a pH of 11 for sodium percarbonate) may not be compatible with plant treatment. These compounds are easy to use, particularly because they make it possible to dispense with the use of concentrated hydrogen peroxide solutions which are well known to be oxidizing, irritant, and able to cause fire or explosion.

In addition, these compounds enable easy application and safe handling. Moreover, on drying, these solutions form a protective antimicrobial biofilm which makes the treated surface more resistant, in particular to bacterial and/or fungal contamination.

Entirely surprisingly, the citrate perhydrates of the invention are physically and chemically stable. On the contrary, concentrated solutions of citric acid and hydrogen peroxide, mixed, do not crystallise in the form of perhydrates and are not chemically stable, in particular regarding the concentration of active oxygen. The compounds of the invention therefore make it possible to stabilise solid concentrated hydrogen peroxide in the form of novel citrate perhydrate molecules.

For example, a solution containing 37.5% hydrogen peroxide and 25% citric acid loses on average 34.4% of its hydrogen peroxide content after 20 days. This instability is the result of the oxidation of the citric acid by the hydrogen peroxide to give dicarboxylic acetone, which is in turn oxidised to give formaldehyde, formic acid and carbon dioxide. A second epoxidation of the citric acid also takes place and gives rise to the formation of percitric acid (example 7).

Thus, according to a first aspect, the invention relates to the use of a citrate perhydrate as biocide.

According to one embodiment, the citrate perhydrate is a citrate perhydrate of alkali, alkaline earth, transition or post-transition metal.

According to an advantageous embodiment, the citrate perhydrate is a citrate perhydrate of alkali metal, the alkali metal being in particular Na or K.

According to one embodiment, when said citrate perhydrate of alkali, alkaline earth, transition or post-transition metal is a trisodium citrate perhydrate or a tripotassium citrate perhydrate, this trisodium citrate perhydrate is not trisodium citrate diperhydrate or tripotassium citrate triperhydrate.

According to one embodiment, the citrate perhydrate of alkali, alkaline earth, transition or post-transition metal is in the form of a crystal formed of citric acid and/or citrate of alkali, alkaline earth, transition or post-transition metal, hydrogen peroxide, and optionally water.

According to an advantageous embodiment, the alkali, alkaline earth, transition or post-transition metal is selected from Li, Na, K, Rb, Cs, Be, Mg, Ca, Sr, Ba, and Zn.

According to a particularly advantageous embodiment, the alkali, alkaline earth, transition or post-transition metal is selected from Ca, Na, K, Mg and Zn, the alkali, alkaline earth, transition or post-transition metal being in particular Na.

In particular, the citrate perhydrate is a disodium citrate perhydrate, a dipotassium citrate perhydrate, a magnesium citrate perhydrate, a zinc citrate perhydrate, or trisodium citrate monoperhydrate dihydrate, in particular an anhydrous disodium citrate monoperhydrate.

According to one embodiment, said citrate perhydrate is in the form of a hydrate, in particular a monohydrate or dihydrate.

According to one embodiment, said citrate perhydrate is a citrate monoperhydrate or a citrate diperhydrate, in particular a citrate monoperhydrate.

According to a particular embodiment, said citrate perhydrate is a disodium citrate monoperhydrate or a dipotassium citrate monoperhydrate, optionally a disodium citrate monoperhydrate co-crystallised with urea perhydrate or a dipotassium citrate monoperhydrate co-crystallised with urea perhydrate.

According to a particular embodiment, said citrate perhydrate is a non-hydrated disodium or dipotassium citrate perhydrate, in particular a non-hydrated disodium citrate perhydrate.

According to a more particular embodiment, said citrate perhydrate is a non-hydrated disodium or potassium citrate monoperhydrate, in particular a non-hydrated disodium citrate monoperhydrate.

According to another particular embodiment, said citrate perhydrate is a trisodium citrate monoperhydrate.

The hydrates of the invention are advantageously readily water soluble, in particular at 25° C., their solubility being in particular greater than or equal to 850 g/l at 25° C.

According to one embodiment, said citrate perhydrate is in the form of a crystal, in particular a crystal hydrate.

According to one embodiment, said citrate perhydrate is used in the absence of N-acyl compounds intended to acylate the hydrogen peroxide.

According to one embodiment, said citrate perhydrate is used in the presence of urea perhydrate.

According to a particular embodiment, said citrate perhydrate is co-crystallised with urea perhydrate.

According to an advantageous embodiment, said citrate perhydrate is in the form of crystals of citrate perhydrate of alkali, alkaline earth, transition or post-transition metals, and is used in the presence of urea perhydrate in crystalline form, these two crystals being in particular in the form of co-crystals.

According to an advantageous embodiment, said citrate perhydrate is a disodium citrate perhydrate, a dipotassium citrate perhydrate, or a disodium citrate perhydrate co-crystallised with urea perhydrate, in particular a disodium citrate perhydrate co-crystallised with urea perhydrate.

In particular, the urea perhydrate is in the form of a urea-hydrogen peroxide co-crystal. The advantage of the combined use of urea perhydrate is the provision of a source of nitrogen while increasing the concentration of hydrogen peroxide. According to one embodiment, said citrate perhydrate is used in the presence of water.

According to one embodiment, said citrate perhydrate is used in the presence of at least one additional compound selected from anti-agglomerating agents, surfactants, in particular biosurfactants, wetting agents, antifoaming agents, anti-drift agents, thickeners, foaming agents, fertilizers, phytopharmaceutical products, stabilisers and mixtures thereof, the additional compound being in particular selected from glycolipids, disodium pyrophosphate, sodium cocoyl isethionate, heptamethyltrisiloxane, disodium silicate, zinc oxides or peroxides and silicon dioxide.

According to a particular embodiment, said citrate perhydrate is used in a mixture with water and optionally at least one additional compound selected from anti-agglomerating agents, surfactants, in particular biosurfactants, wetting agents, antifoaming agents, anti-drift agents, thickeners, foaming agents, solidifying agents, fertilizers, phytopharmaceutical products, stabilisers and mixtures thereof, the additional compound being in particular selected from glycolipids, disodium pyrophosphate, sodium cocoyl isethionate, heptamethyltrisiloxane, disodium silicate, zinc oxides or peroxides and silicon dioxide, the percentage by weight of said citrate perhydrate of alkali, alkaline earth, transition or post-transition metal relative to the total weight of said mixture being in particular from 0.05 to 5%.

More particularly, the percentage by weight of said citrate perhydrate relative to the total weight of said mixture is from 0.1 to 2, 2.5, 3, 3.5, 4 or 4.5%.

Such additional compounds are well known to the person skilled in the art. They may be pre-formulated as a mixture with citrate perhydrate, or added to the mixture obtained by bringing the citrate perhydrate into contact with water.

According to a particular embodiment, said at least one additional compound is selected from the group comprising urea citrate, a co-crystal of citric acid and urea, optionally perhydrated, and urea perhydrate, in particular in crystalline form. The compounds of this group make it possible in particular to adjust the pH and/or adjust the content of hydrogen peroxide and/or adjust the provision of nitrogen during the use of the citrate perhydrates of the invention.

When the compound of the invention is a magnesium citrate perhydrate and/or is used in the presence of a compound comprising magnesium, these compounds are additionally used as fertiliser, in particular foliar fertiliser, or as soil enricher.

The stabilisers are in particular peroxide stabilisers. These stabilisers are well known to the person skilled in the art, in particular as hydrogen peroxide stabilisers.

The addition of a foaming agent may make it possible to obtain a mixture according to the invention in the form of a foam. The foams may be used on surfaces.

The addition of a thickener may make it possible to obtain a mixture according to the invention in the form of a gel. The gels may be used on the skin of humans or animals, in particular the hands.

The addition of a solidifying agent may make it possible to obtain a mixture according to the invention in the form of a solid. The solids may be used to treat water, in particular in swimming pools and toilets.

According to an advantageous embodiment, said additional compound is selected from glycolipids, in particular rhamnolipids.

These rhamnolipids may be obtained according to techniques well known to the person skilled in the art, in particular by culturing bacteria of the genus *Pseudomonas* in the presence of molasses.

Within the compositions of the present invention, glycolipids, in particular rhamnolipids, have advantageous elicitor and biosurfactant properties.

According to one embodiment, the use as defined above is a use for inhibiting the growth of a pathogen on or in a plant.

Thus, the present invention also relates to the use of a compound as described previously or of a composition as described previously as inhibitor of the growth of a pathogen on or in a plant.

Figure 7:
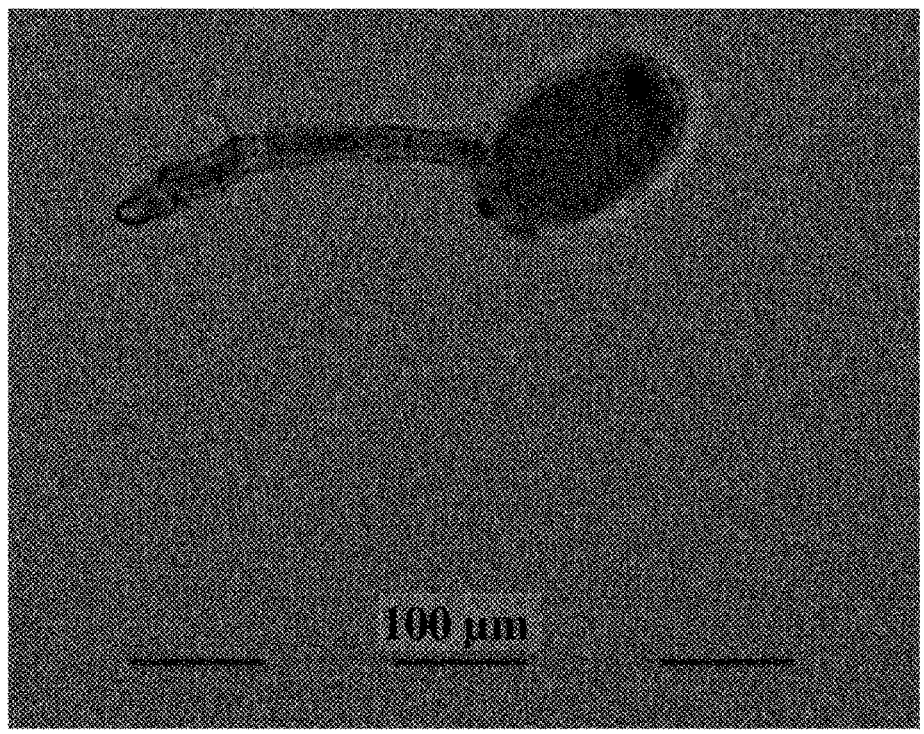
Figure 7:
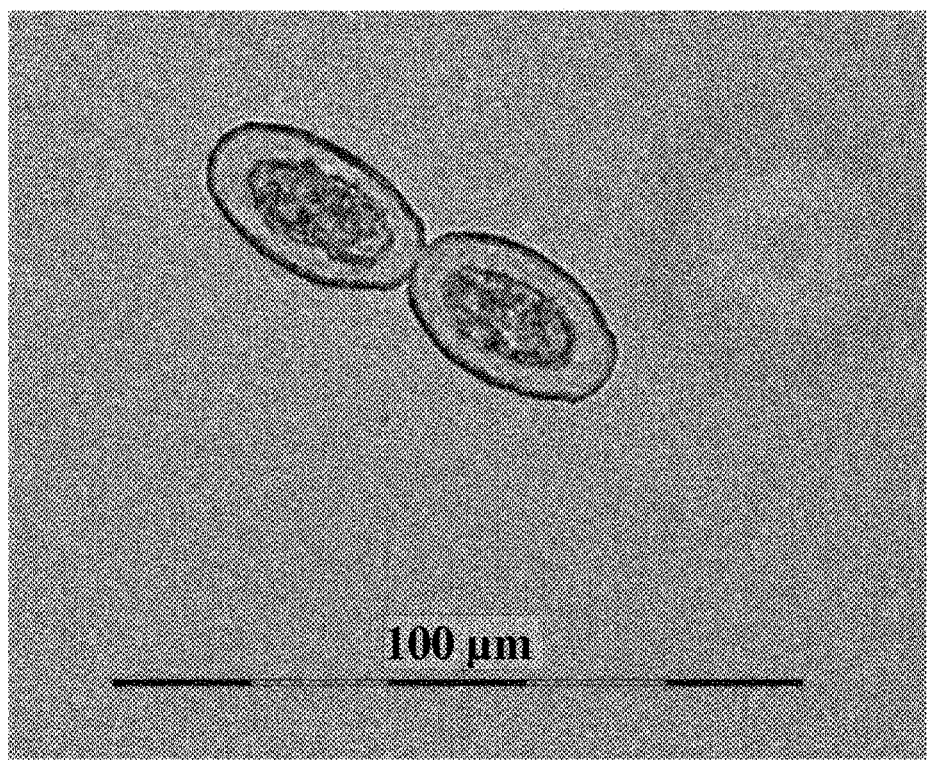

Without wishing to be bound by a particular theory, said citrate perhydrate causes oxidative, ionic and osmotic stress to the targeted pathogen and causes the shrinkage of its cellular contents in the case, for example, of the pathogen *Erysiphe necator*, as illustrated in FIG. 7.

According to one embodiment, the use as defined above is a use for preventing the growth of a pathogen on or in a plant.

Thus, the present invention relates to the use of a compound as described previously or of a composition as described previously in the prevention of the growth of a pathogen on or in a plant.

Without wishing to be bound by a particular theory, the prevention comes about due to the tacky properties ascribed to the citrates and/or to the optional added tackifiers, which results in the formation of a protective barrier around the treated surface, preventing, for example, spore propagation.

In particular, said citrate perhydrate is applied to the surface of the plant, in particular in an amount of 25 to 1000 ng·dm$^{-2}$.

According to one embodiment, said citrate perhydrate, optionally used in the presence of water, is applied to the surface of the plant by spraying, vaporising, soaking, painting, fumigating or electrostatic spraying, preferably by spraying, in particular by foliar spraying.

According to one embodiment, said citrate perhydrate, optionally used in the absence of water, is applied to the roots of the plant or in the soil in contact with the roots of the plant. According to one embodiment, the pathogen is selected from viruses, bacteria, fungi and pseudofungi.

According to a particular embodiment, the pathogen is a fungus or pseudofungus selected from *Albugo* spp., *Alternaria* spp., *Armillaria* spp., *Aspergillus* spp., *Athelia* spp., *Bipolaris* spp., *Botryosphaeria* spp., *Botryotinia* spp., *Botrytis* spp., *Bremia* spp., *Candida* spp., *Capnodium* spp., *Ceratobasidium* spp., *Ceratocystis* spp., *Cercospora* spp., *Choanephora* spp., *Claviceps* spp., *Corynespora* spp., *Cronartium* spp., *Cryphonectria* spp., *Cylindrocladium* spp., *Cytospora* spp., *Diaporthe* spp., *Diplodia* spp., *Dreschlera* spp., *Elsinoe* spp., *Erexohilum* spp., *Erysiphe* spp., *Eutypa* spp., *Exobasidium* spp., *Fusarium* spp., *Gaeumannomyces* spp., *Gliocladium* spp., *Gymnosporangium* spp., *Heterobasidium* spp., *Hypoxylon* spp., *Kutilakesa* spp., *Lophiodermium* spp., *Magnaporthe* spp., *Melampsora* spp., *Monilinia* spp., *Mycosphaerella* spp., *Myrothecia* spp., *Nectriella* spp., *Nematospora* spp., *Oiâium* spp., *Olpidium* spp., *Ophiostoma* spp., *Penicillium* spp., *Peronospora* spp., *Phakospora* spp., *Phoma* spp., *Phomopsis* spp., *Phragmidium* spp., *Phyllactinia* spp., *Physoderma* spp., *Phytophthora* spp., *Plasmodiophora* spp., *Plasmopara* spp., *Pseudoperonospora* spp., *Puccinia* spp., *Pythium* spp., *Rhizoctonia* spp., *Rhizopus* spp., *Rhytisma* spp., *Sclerotinia* spp., *Sclerotium* spp., *Spongospora* spp., *Synchytrium* spp., *Taphrina* spp., *Thanatephorus* spp., *Thielaviopsis* spp., *Tilletia* spp., *Uncinula* spp., *Urocystis* spp., *Ustilago* spp., *Valsa* spp., *Venturia* spp., *Verticillium* spp., *Xylaria* spp, *Fomitiporia* spp., *Stereum* spp., *Phaeoacremonium* spp. and *Phaeomoniella* spp.

According to an even more particular embodiment, the pathogen is a fungus or pseudofungus selected from *Plasmopara* spp., *Erysiphe* spp., *Botrytis* spp., *Aspergillus* spp. and *Candida* spp.

According to a particular embodiment, the pathogen is a bacterium selected from bacteria of the genera *Pseudomonas, Escherichia, Staphylococcus, Enterococcus*, and *Legionella*.

According to a particular embodiment, the pathogen is one or more microorganisms selected from *Candidatus phytoplasma, Fomitiporia punctata, F. mediteranea, Stereum hirsutum, Phaeoacremonium aleophilium, Phaeomoniella chlamydospora, Botryosphaeria obtusa, Botryosphaeria dothidea parva* and *stevensii*, and *Eutypa lata*.

According to one embodiment, the plant is selected from fruit-bearing plants, vegetable-bearing plants, ornamental plants, turf and cereals.

Ornamental plant is intended to mean in particular a plant grown for its decorative qualities.

Turf is intended to mean in particular all grasses, in particular Gramineae, which form or are included in lawns.

According to a particular embodiment, the plant produces fruit selected from apples, apricots, bananas, blackberries, blackcurrants, cherries, cranberries, redcurrants, eating grapes, wine grapes (the plant being in particular a vine), pomegranates, melons, lemons, mandarins, oranges, peaches, pears, pineapples, plums, raspberries, strawberries, tomatoes, watermelons, grapefruit, pepper, olives, limes, almonds, walnuts, Brazil nuts, cashew nuts, chestnuts, hazelnuts, macadamia nuts, pecans and pistachios.

According to a particular embodiment, the plant produces vegetables selected from artichokes, beans, beets, broccoli, cabbages, carrots, cauliflowers, celery, endives, chives, watercress, cucumbers, kale, aubergines, kohlrabi, lettuce, onions, peppers, parsnips, parsley, peas, potatoes, pumpkin, radish, shallots, soya, spinach, turnips and peanuts.

According to a particular embodiment, the plant is a cereal, in particular in the form of stubble.

According to a particular embodiment, the plant is a cereal selected from amaranth, barley, buckwheat, fonio, kamut (Khorasan wheat), millet, oats, quinoa, rice, rye, sorghum, spelt, triticale, wheat or rapeseed.

According to one embodiment, the present invention also relates to the use of a compound as described previously or of a composition as described previously as a biocontrol element.

According to one embodiment, the present invention relates to the use of a citrate perhydrate for disinfecting a fluid or a surface, in particular water, air, floors, swimming pools, work surfaces, toilets.

According to one embodiment, the present invention relates to the use of a citrate perhydrate for disinfecting a fluid, in particular water or air, by reducing in particular the number of viable bacterial cells, the bacterial cells being in particular of the genus *Legionella*, more particularly *L. pneumophila*.

Thus, said citrate perhydrate may be used as a disinfectant for a fluid or for a surface.

Facilities such as spas, swimming pools, cooling towers, food-processing plants, healthcare settings, are able to be disinfected by a compound as described previously or a composition as described previously.

According to another embodiment, the present invention relates to the use of a citrate perhydrate for disinfecting a surface, in particular in community settings, in healthcare settings or in food-processing plants, in particular the floors, work surfaces, and toilets.

According to one embodiment, the present invention relates to the use of a citrate perhydrate for disinfecting a surface, by reducing in particular the number of viable bacterial cells or fungi, the bacterial cells being in particular selected from *Pseudomonas aeruginosa, Escherichia coli, Staphylococcus aureus, Enterococcus hirae*, and the fungi being in particular selected from *Candida albicans* and *Aspergillus niger*.

According to one embodiment, the present invention relates to the use of a citrate perhydrate as defined previously as an elicitor.

According to another aspect, the present invention relates to a citrate perhydrate for use thereof as an antimicrobial agent in humans or animals.

It should be noted that all the embodiments mentioned above in relation to the citrate perhydrate also apply here, alone or in combination.

According to a particular embodiment, the citrate perhydrate is used in dentistry.

According to another particular embodiment, the citrate perhydrate is used in animals, in particular for the treatment of udders, in particular of cows, or feet, in particular of horses.

According to another aspect, the present invention relates to a method of tooth whitening by bringing teeth into contact with a citrate perhydrate.

According to another aspect, the present invention relates to a citrate perhydrate as described previously, for use thereof in dentistry, in particular in tooth whitening.

It should be noted that all the embodiments mentioned above in relation to the citrate perhydrate also apply here, alone or in combination.

According to one embodiment, the present invention relates to a citrate perhydrate for use thereof as a bactericide or a bacteriostat, in particular for bacteria selected from *Pseudomonas aeruginosa, Escherichia coli, Staphylococcus aureus, Enterococcus hirae*.

According to one embodiment, said use is topical.

According to another aspect, the present invention relates to a pharmaceutical composition formed of or comprising a citrate perhydrate and a pharmaceutically acceptable excipient.

It should be noted that all the embodiments mentioned above in relation to the citrate perhydrate also apply here, alone or in combination.

According to another aspect, the present invention relates to a citrate perhydrate of alkali, alkaline earth, transition or post-transition metal with the proviso that, when said citrate perhydrate of alkali, alkaline earth, transition or post-transition metal is a trisodium citrate perhydrate or a tripotassium citrate perhydrate, this trisodium citrate perhydrate is not trisodium citrate diperhydrate or tripotassium citrate triperhydrate.

According to an advantageous embodiment, the present invention relates to a citrate perhydrate of alkali, alkaline earth, transition or post-transition metal, with the proviso that:
  when the alkali, alkaline earth, transition or post-transition metal is sodium, said citrate is a disodium citrate perhydrate or a trisodium citrate perhydrate, in particular a trisodium citrate perhydrate;
  when said citrate perhydrate of alkali, alkaline earth, transition or post-transition metal is a trisodium citrate perhydrate or a tripotassium citrate perhydrate, this trisodium citrate perhydrate is not trisodium citrate diperhydrate or tripotassium citrate triperhydrate.

According to an advantageous embodiment, the alkali, alkaline earth, transition or post-transition metal is selected from Li, Na, K, Rb, Cs, Be, Mg, Ca, Sr, Ba, and Zn.

According to a particularly advantageous embodiment, the alkali, alkaline earth, transition or post-transition metal is selected from Ca, Na, K, Mg and Zn, the alkali, alkaline earth, transition or post-transition metal being in particular Na.

According to one embodiment, the citrate perhydrate of alkali, alkaline earth, transition or post-transition metal is a di-alkali metal citrate perhydrate.

According to one embodiment, the citrate perhydrate of alkali, alkaline earth, transition or post-transition metal is a disodium citrate perhydrate, a dipotassium citrate perhydrate, a magnesium citrate perhydrate, in particular a trimagnesium dicitrate perhydrate, a zinc citrate perhydrate, in particular a trizinc dicitrate perhydrate, or trisodium citrate monoperhydrate dihydrate.

In particular, the citrate perhydrate is a disodium citrate perhydrate or a dipotassium citrate perhydrate, in particular a disodium citrate perhydrate.

According to one embodiment, said citrate perhydrate is a citrate monoperhydrate or a citrate diperhydrate, in particular a citrate monoperhydrate.

According to a particular embodiment, said citrate perhydrate is a disodium citrate monoperhydrate or a dipotassium citrate monoperhydrate.

According to another particular embodiment, said citrate perhydrate is a trisodium citrate monoperhydrate.

According to one embodiment, the citrate perhydrate of alkali, alkaline earth, transition or post-transition metal is in the form of a crystal formed of citric acid and/or alkali metal citrate, hydrogen peroxide, and optionally water.

According to one embodiment, the citrate perhydrate of alkali, alkaline earth, transition or post-transition metal is in the form of a hydrate.

The citrate perhydrates of the invention may be single crystals. Indeed, the signature obtained by X-ray diffractometry is unique to them. These crystals are in particular distinguished by the number and nature of the alkali, alkaline earth, transition or post-transition metals, by the number of adducts of hydrogen peroxide molecules and by the number of adducts of water molecules.

According to one embodiment, the citrate perhydrate of alkali, alkaline earth, transition or post-transition metal is a trisodium citrate monoperhydrate dihydrate having an X-ray diffraction spectrum with the following characteristic lines at the 2θ angles (in °), in particular the characteristic lines for which the relative intensity is greater than or equal to 20:

| Peaks | 2θ | Relative intensity | hkl index |
|---|---|---|---|
| 1 | 9.924509 | 100 | 0 0 1 |
| 2 | 8.740994 | 5.95 | 0 1 0 and 0 1 -1 |
| 3 | 6.148828 | 0.87 | 1 0 0 |
| 4 | 5.519614 | 15.76 | -1 0 1 |
| 5 | 5.483783 | 36.95 | 0 -1 2 |
| 6 | 5.372527 | 51.54 | -1 1 0 |
| 7 | 4.959513 | 16.42 | -1 -1 1 and 0 0 2 |
| 8 | 4.871902 | 5.55 | 0 -2 1 |
| 9 | 4.740059 | 4.39 | 1 1 0 |
| 10 | 4.413263 | 36.26 | -1 1 1 |
| 11 | 4.381867 | 6.14 | 0 -2 2 |
| 12 | 4.364081 | 19.23 | 0 2 0 |
| 13 | 4.094722 | 2.37 | -1 0 2 |
| 14 | 4.000887 | 38.77 | 1 -2 1 and 1 -1 2 |
| 15 | 3.679708 | 4.92 | 0 -1 3 |
| 16 | 3.660295 | 10.8 | 1 0 2 and -1 -2 1 |
| 17 | 3.62327 | 22.99 | 1 -2 2 |
| 18 | 3.514807 | 11.02 | -1 -2 2 |
| 19 | 3.483591 | 3.3 | 0 -2 3 |
| 20 | 3.466081 | 14.3 | 0 2 1 |

According to one embodiment, the citrate perhydrate of alkali, alkaline earth, transition or post-transition metal is a disodium citrate perhydrate having an X-ray diffraction spectrum with the following characteristic lines at the 2θ angles (in °), in particular the characteristic lines for which the relative intensity is greater than or equal to 15:

| Peaks | 2θ | Relative intensity | hkl index |
|---|---|---|---|
| 1 | 7.10442 | 2.42 | 0 0 1 |
| 2 | 6.53808 | 6.93 | 1 1 1 |
| 3 | 6.19763 | 11.5 | 0 2 0 |
| 4 | 5.03008 | 18.94 | 2 2 0 |
| 5 | 4.83206 | 0.76 | 1 2 1 |
| 6 | 4.45527 | 10.07 | 3 1 1 |
| 7 | 4.34762 | 32.9 | 2 2 1 |
| 8 | 4.29193 | 11.19 | 4 0 0 |
| 9 | 4.21333 | 17.21 | 3 2 0 |
| 10 | 3.97003 | 19.47 | 1 1 2 |
| 11 | 3.85293 | 13.47 | 4 0 1 and 2 0 2 |
| 12 | 3.78756 | 19.04 | 3 2 1 |
| 13 | 3.67804 | 12.75 | 4 1 1 |
| 14 | 3.53769 | 100 | 4 2 0 |
| 15 | 3.47303 | 5.61 | 1 2 2 |
| 16 | 3.42705 | 7.44 | 2 3 1 |
| 17 | 3.32368 | 6.66 | 3 1 2 |
| 18 | 3.2801 | 32.86 | 2 2 2 |
| 19 | 3.13095 | 31.11 | 3 3 1 |
| 20 | 3.09689 | 19.5 | 5 1 1 |

According to an advantageous embodiment, said citrate perhydrate is a disodium citrate perhydrate, a dipotassium citrate perhydrate, or a disodium citrate perhydrate co-crystallised with urea perhydrate, in particular a disodium citrate perhydrate co-crystallised with urea perhydrate.

According to another aspect, the invention also relates to a composition formed of or comprising a citrate perhydrate as defined previously, in particular a disodium citrate perhydrate, and urea perhydrate.

According to one advantageous embodiment, said citrate perhydrate is a disodium citrate perhydrate.

In particular, the urea perhydrate is in the form of a urea-hydrogen peroxide co-crystal.

According to an advantageous embodiment, the invention relates to a composition comprising crystals of disodium citrate perhydrate or of dipotassium citrate perhydrate, and crystals of urea perhydrate, in particular in the form of a urea-hydrogen peroxide co-crystal. The crystals of disodium citrate perhydrate or of dipotassium citrate perhydrate and those of urea perhydrate are in particular co-crystallised.

According to another aspect, the invention relates to a method for preparing a citrate perhydrate of alkali, alkaline earth, transition or post-transition metal as defined previously, said method comprising:

(i) a step of bringing a citrate of alkali, alkaline earth, transition or post-transition metal into contact with hydrogen peroxide, to obtain said citrate perhydrate of alkali, alkaline earth, transition or post-transition metal.

Preferably, the amounts of citrate of alkali, alkaline earth, transition or post-transition metal and of hydrogen peroxide are stoichiometric, according to the composition of the desired citrate perhydrate of alkali, alkaline earth, transition or post-transition metal.

The stoichiometric amounts are for example implemented using a gravimetric feeder.

According to an advantageous embodiment, the citrate of alkali, alkaline earth, transition or post-transition metal is in solid form, in particular anhydrous, and the hydrogen peroxide is in the form of an aqueous solution of hydrogen peroxide at a concentration of from 30 to 80% by weight.

Step (i) is in particular carried out at a temperature of from 30 to 90° C., in particular from 40 to 80° C., more particularly from 50 to 70° C., in particular from 55 to 65° C.

According to a highly advantageous embodiment, the contacting is carried out using an extruder, for example a twin-screw extruder.

According to another advantageous embodiment, the composition obtained in step (i) is introduced into an alcohol or an alcohol-based solution, said alcohol being in particular a C1 to C5 alcohol. The use of this alcohol may in particular make it possible to obtain the precipitation of the desired citrate perhydrate, which can be isolated by well-known liquid-solid separation techniques.

According to a highly advantageous embodiment, the contacting is carried out by mixing an aqueous solution containing a citrate of alkali, alkaline earth, transition or post-transition metal and hydrogen peroxide; and alcohol or alcohol-based solution, the volume ratio of the alcohol or the alcohol-based solution to the aqueous solution being in particular from 3.7:1 to 8:1.

According to one embodiment, step (i) is preceded by a step of neutralisation of a citric acid with a hydroxide, a carbonate or a citrate of alkali, alkaline earth, transition or post-transition metal, in order to obtain the citrate of alkali, alkaline earth, transition or post-transition metal as mentioned in step (i).

This neutralisation step may be total or partial.

According to another embodiment, a step of neutralisation of a citric acid with a hydroxide, a carbonate or a citrate of alkali, alkaline earth, transition or post-transition metal, in order to obtain the citrate of alkali, alkaline earth, transition or post-transition metal as mentioned in step (i), is carried out concomitantly with this step (i).

In particular, the invention relates to a method for preparing a citrate perhydrate of alkali, alkaline earth, transition or post-transition metal as defined previously, said method comprising:

(i') a step of bringing into contact citric acid; a hydroxide, carbonate or citrate of alkali, alkaline earth, transition or post-transition metal; and hydrogen peroxide, to obtain said citrate perhydrate of alkali, alkaline earth, transition or post-transition metal.

The hydroxide, carbonate or citrate of alkali, alkaline earth, transition or post-transition metal is in particular a citrate of alkali, alkaline earth, transition or post-transition metal.

Preferably, the amounts of citric acid/citrate, of alkali, alkaline earth, transition or post-transition metal and of hydrogen peroxide are stoichiometric, according to the composition of the desired citrate perhydrate of alkali, alkaline earth, transition or post-transition metal.

According to a particular embodiment, step (i) or (i') as defined previously is followed by a step of drying and/or grinding.

These steps may be carried out according to techniques well known to the person skilled in the art.

According to another aspect, the invention relates to a method for preparing a composition formed of or comprising a citrate perhydrate as defined previously, and urea perhydrate, in particular as defined previously, said method comprising a step (a) of co-crystallisation by bringing into contact a citrate of alkali, alkaline earth, transition or post-transition metal; urea; and hydrogen peroxide.

Preferably, the amounts of citrate of alkali, alkaline earth, transition or post-transition metal and of hydrogen peroxide are stoichiometric, according to the composition of the desired citrate perhydrate of alkali, alkaline earth, transition or post-transition metal.

Preferably, the amount of urea is from 1 to 5 mol of urea per mole of citric acid salt, preferably from 2 to 4 mol of urea per mole of citric acid salt, in particular 3 mol of urea per mole of citric acid salt.

According to an advantageous embodiment, the citrate of alkali, alkaline earth, transition or post-transition metal and the urea are in solid form, and the hydrogen peroxide is in the form of an aqueous solution of hydrogen peroxide at a concentration of from 30 to 80% by weight.

Step (a) is in particular carried out at a temperature of from 30 to 90° C., in particular from 40 to 80° C., more particularly from 50 to 70° C., in particular from 55 to 65° C.

According to a highly advantageous embodiment, the contacting is carried out using an extruder, for example a twin-screw extruder.

For example, in the case of producing a co-crystallisation of 1 mol of trisodium citrate monoperhydrate dihydrate and 3 mol of urea perhydrate, 4 mol of hydrogen peroxide are added to 1 mol of trisodium citrate and 3 mol of urea.

According to one embodiment, step (a) is preceded by a step of neutralisation of a citric acid with a hydroxide, a carbonate or a citrate of alkali, alkaline earth, transition or post-transition metal, in order to obtain the citrate of alkali, alkaline earth, transition or post-transition metal as mentioned in step (a).

This neutralisation step may be total or partial.

According to another embodiment, a step of neutralisation of a citric acid with a hydroxide, a carbonate or a citrate of alkali, alkaline earth, transition or post-transition metal, in order to obtain the citrate of alkali, alkaline earth, transition or post-transition metal as mentioned in step (a), is carried out concomitantly with this step (a).

In particular, the invention relates to a method for preparing a composition formed of or comprising a citrate perhydrate as defined previously, and urea perhydrate, in particular as defined previously, said method comprising:

(a') a step of bringing into contact citric acid; a hydroxide, carbonate or citrate of alkali, alkaline earth, transition or post-transition metal; urea; and hydrogen peroxide, to obtain said citrate perhydrate of alkali, alkaline earth, transition or post-transition metal.

The hydroxide, carbonate or citrate of alkali, alkaline earth, transition or post-transition metal is in particular a citrate of alkali, alkaline earth, transition or post-transition metal.

Preferably, the amounts of citrate of alkali, alkaline earth, transition or post-transition metal and of hydrogen peroxide are stoichiometric, according to the composition of the desired citrate perhydrate of alkali, alkaline earth, transition or post-transition metal.

Preferably, the amount of urea is from 1 to 5 mol of urea per mole of citric acid salt, preferably from 2 to 4 mol of urea per mole of citric acid salt, in particular 3 mol of urea per mole of citric acid salt.

According to a particular embodiment, step (a) or (a') as defined previously is followed by a step of drying and/or grinding.

These steps may be carried out according to techniques well known to the person skilled in the art.

Definitions

As it is used in the present description, the term "approximately" refers to a range of values ±10% of a specific value. By way of example, the expression "approximately 120 mg" includes values of 120 mg±10%, i.e. values from 108 mg to 132 mg.

For the purposes of the present description, the percentages refer to percentages by weight relative to the total weight of the formulation, unless indicated otherwise.

As it is intended here, ranges of values in the form "x-y" or "from x to y" or "between x and y" include the limit values x and y and also the integers contained between these limit values. By way of example, "1-5" or "from 1 to 5" or "between 1 and 5" denote the integers 1, 2, 3, 4 and 5. The preferred embodiments include each integer taken individually within the range of values, and also any sub-combination of these integers. By way of example, the preferred values for "1-5" may include the integers 1, 2, 3, 4, 5, 1-2, 1-3, 1-4, 1-5, 2-3, 2-4, 2-5, etc.

"Citrate" is intended to mean a citric acid salt, that is to say that at least one of the three carboxylic acid groups of the citric acid, in particular two of the three, or all three carboxylic acid groups of the citric acid, is in salt form, in particular alkali, alkaline earth, transition or post-transition metal salt.

As examples of salts, mention may be made of salts with alkali metals (sodium, potassium, lithium), with alkaline earth metals (magnesium, calcium), with transition metals, with post-transition metals (zinc), ammonium salt, urea salt, nitrogen-based salts (ethanolamine, diethanolamine, trimethylamine, triethylamine, methylamine, propylamine, diisopropylamine, NN-dimethylethanolamine, benzylamine, dicyclohexylamine, N-benzyl-p-phenethylamine, NN'-dibenzylethylenediamine, diphenylenediamine, benzhydrylamine, quinine, choline, arginine, lysine, leucine, dibenzylamine).

"Citrate perhydrate" (or perhydrated citrate, or citrate peroxyhydrate, or peroxyhydrated citrate, or citrate peroxosolvate, these terms being equivalent here) is intended to mean in particular an adduct between a citrate and hydrogen peroxide, the citrate and the hydrogen peroxide being more particularly bonded, within the same solid, even more particularly within the same crystal, by hydrogen bonds. Thus, the term "citrate perhydrate" preferably does not denote an optionally hydrated percitrate.

Thus, a citrate perhydrate of the invention is in particular of the following formula (I):

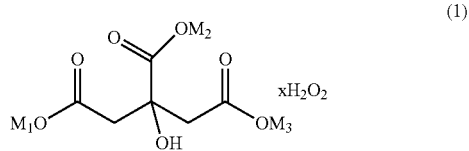

(1)

wherein x is strictly greater than 0, x being in particular 1 or 2, and $M_1$, $M_2$ and $M_3$ represent, independently of one another, H or an atom or compound capable of forming a salt with a carboxylic acid group, in particular an alkali, alkaline earth, transition or post-transition metal, in particular an alkali metal, at least one of $M_1$, $M_2$ and $M_3$ not representing H. It should be noted that this formula (I) may be combined with any other preceding definition or embodiment.

Post-transition metal is intended in particular to mean a metallic chemical element located in the periodic table between the transition metals to their left and the metalloids onto their right. By way of example, the post-transition metal may be zinc.

In particular, only one of the groups $M_1$, $M_2$ and $M_3$ represents H. If, for example, M=Na, reference is made to disodium.

In particular, none of the groups $M_1$, $M_2$ and $M_3$ represent H. If, for example, M=Na, reference is made to trisodium.

In particular, two of the groups $M_1$, $M_2$ and $M_3$ represent H. If, for example, M=Na, reference is made to monosodium.

When $M_1$, $M_2$ and/or $M_3$ represent an alkaline earth, transition or post-transition metal, this metal may be further bonded to another carboxylate, present on the same citrate or on another citrate of formula (I).

For example, one of $M_1$, $M_2$ and $M_3$ represents an alkaline earth metal, the two others being H. In this case, the corresponding citrate of formula (I) is in particular of formula $(C_6H_7O_7)$(alkaline earth metal)$_{1/2}$·x $H_2O_2$.

"Biocide" is intended to mean pesticides and also antimicrobial agents for medical, veterinary, domestic or industrial use, and disinfectants for fluids and surfaces, in particular for water, air, floors, swimming pools, work surfaces, toilets, etc.

Unless otherwise indicated, "surface" is intended in particular to mean the surfaces of living tissues, in particular the surface of plants (for example leaf surfaces), and skin (of humans or animals), and also inert surfaces, in particular organic or inorganic inert surfaces, for example floors and work surfaces.

In the case of pesticides, the surface in question is in particular that of a plant.

In the case of antimicrobial agents, the surface in question is in particular that of human or animal skin.

In the case of disinfectants, the surface in question is in particular an inert surface.

"Pesticide" is intended to mean a chemical substance able to be used to combat organisms which are considered to be harmful. It is a generic term which covers insecticides, fungicides, herbicides and parasiticides. They attack, respectively, pest insects, fungi, "weeds", and parasitic worms.

"Phytopharmaceutical composition" is intended to mean a plant-protection product, i.e. any product intended to:
protect plants or plant products against all harmful organisms, or prevent the action of same;
act on the biological processes of the plants, as long as they are not nutritive substances (for example growth regulators);
ensure the preservation of plant products;
destroy unwanted plants; and/or
destroy parts of plants, arrest or prevent unwanted growth of the plants.

"Antimicrobial agent" is intended to mean a substance which kills or slows the growth of microbes such as bacteria, fungi, viruses or parasites, in particular in humans or animals.

"Disinfectant" is intended to mean a product which kills or inactivates microorganisms such as bacteria, viruses and protozoa, on inert surfaces or within fluids such as water and air.

"Hydrate" is intended to mean a compound formed in particular by the joining of a citrate perhydrate and water. The hydrate is in particular a crystallised salt. Reference is then made to water of crystallisation.

"Non-hydrated" is intended to mean a compound devoid of water of crystallisation.

"Biosurfactant" is intended to mean a surfactant synthesised by a living organism.

"Pseudofungi" is intended to mean organisms selected in particular from Oomycetes, Hyphochytridiomycetes and Labyrinthulomycetes.

"Stubble" is intended to mean the remainder of a crop formed of the parts of the cereal stalks left on the ground after harvesting.

"Elicitor" is intended to mean a compound or composition which triggers plant defence mechanisms with production of defensive substances. It is a stimulator of the natural defences (SND) of the plant.

As it is used here, the term "pharmaceutically acceptable" refers to compounds, compositions and/or dosage forms which are, within the scope of a valid medical judgement, suitable for use in contact with cells of humans and lower animals without toxicity, irritation, induced allergic reaction and the like, and which are proportionate to a reasonable benefit/risk ratio.

Throughout this description, and unless indicated otherwise, the terms "sodium, disodium, trisodium citrate" are interchangeable with the terms "citrate (of) sodium, disodium, trisodium", respectively. The same applies for the other metals.

"Co-crystallised" is intended to mean in particular two crystals of different compounds, obtained from a solution, in particular by evaporation of the latter, comprising these two compounds. At least one of these two compounds may be in the form of a co-crystal.

Thus, in particular, co-crystallised crystals form a composition in which two crystals of different natures co-exist, unlike a co-crystal which is one and the same crystal comprising or formed of two different compounds.

FIGURES

FIG. 1 shows the distribution graph for citric acid and the salts thereof.

Figure 2:
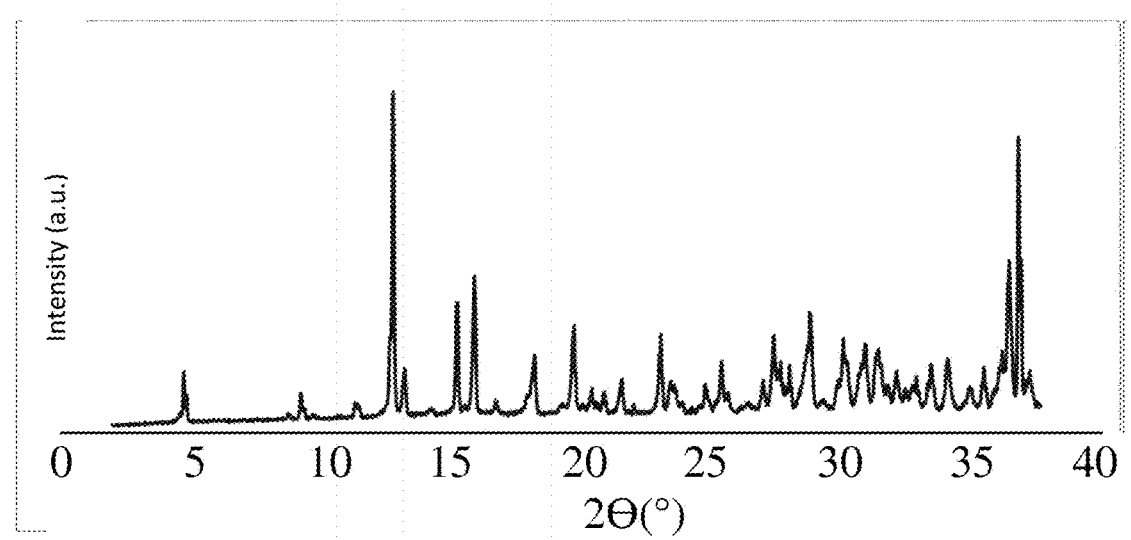

FIG. 2 corresponds to the powder graph for the trisodium citrate monoperhydrate dihydrate of example 2 ($\lambda$=1.5418 Å).

Figure 3:
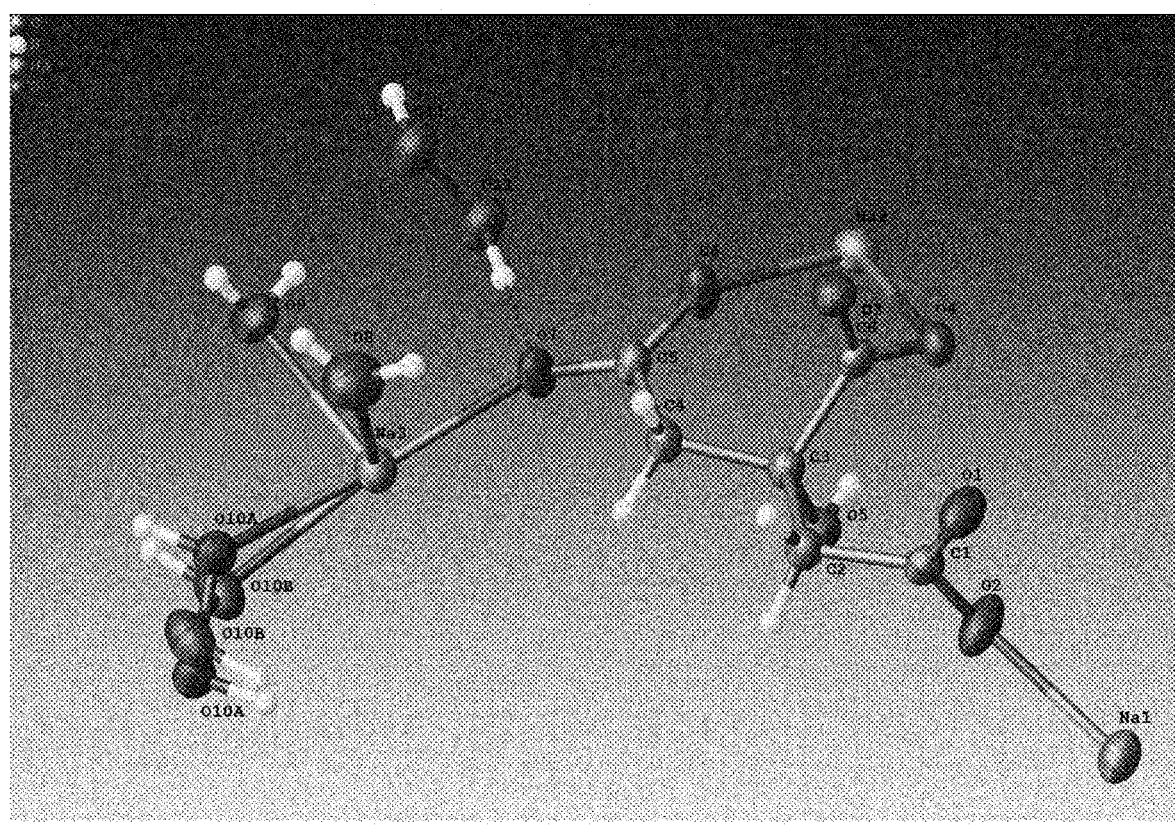

FIG. 3 shows the asymmetric unit and the schematic labelling of the trisodium citrate monoperhydrate dihydrate of example 2.

Figure 4:
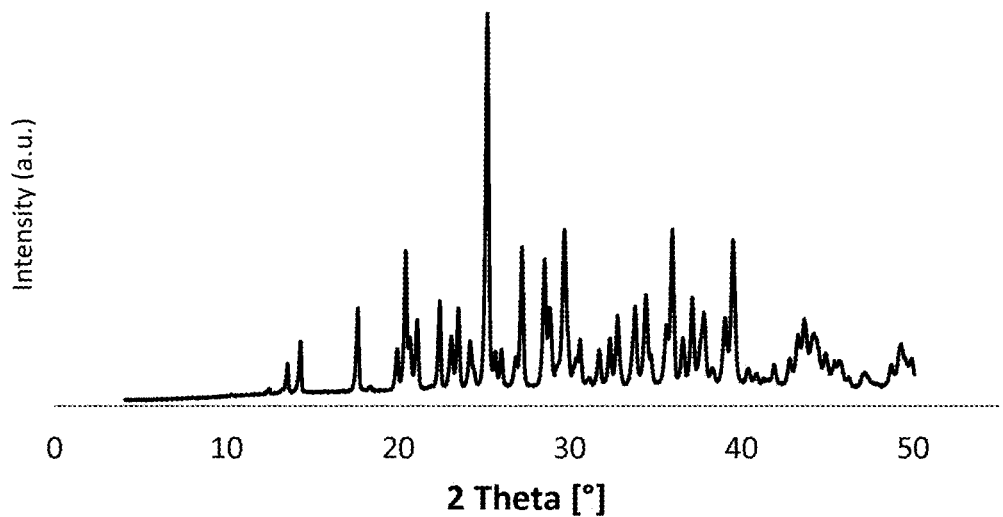

FIG. 4 corresponds to the powder graph for the disodium citrate perhydrate of example 3 ($\lambda$, =1.5418 Å).

Figure 5:
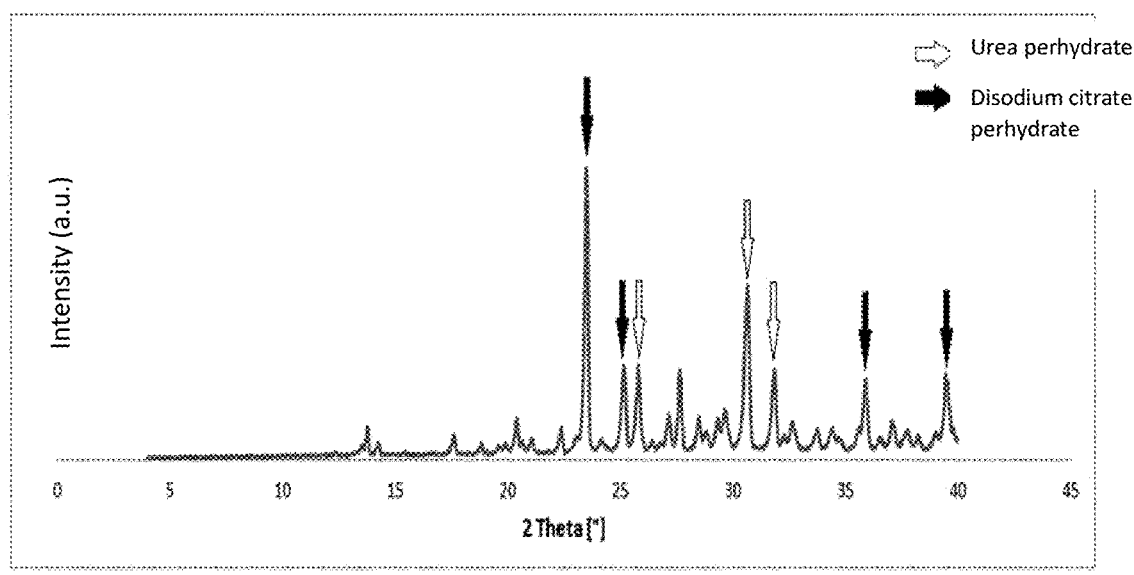

FIG. 5 illustrates the diffractogram of the co-crystallisation of one mole of disodium citrate perhydrate and 3 mol of urea perhydrate ($\lambda$=1.5418 Å) according to example 4.

Figure 6:
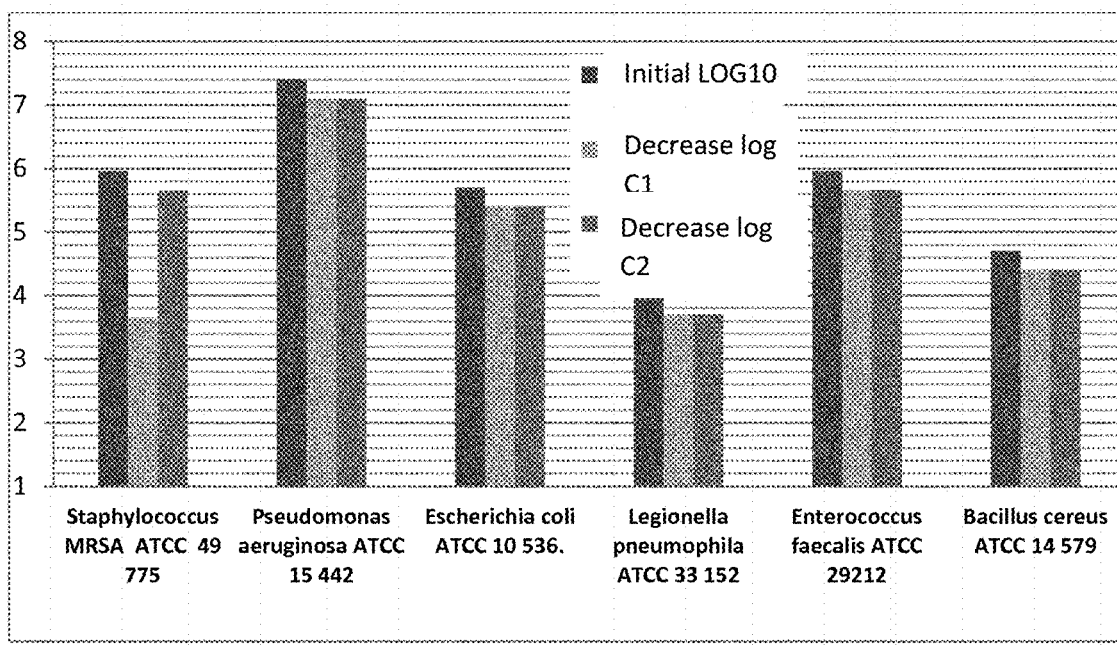

FIG. 6 corresponds to the logarithmic concentration of the different pathogenic strains initially present, and the logarithmic decrease in the strains after treatment with formulation 3 at a hydrogen peroxide concentration C1 (=0.5%) and C2 (=3%).

FIG. 7 corresponds to micrographs of the fungus *Erysiphe necator*.

FIG. 7A: in water. FIG. 7B: in the presence of citrate perhydrate (10 mg/ml).

FIG. 8 illustrates the results obtained during the field evaluation of the efficacy of formulation 3 of the invention for the treatment of powdery mildew according to example 5.5. The percentage incidence and severity of the disease is given both for leaves (FIG. 8A) and for grapes (FIG. 8B).

EXAMPLES

Example 1: Synthesis of Citrate Perhydrates

A method for preparing the citrate perhydrates of the present invention consists in crystallising hydrogen peroxide with a salt of citric acid.

Only citrate perhydrates which form the subject matter of the present invention can be produced using the preparation method presented below.

The equipment likely to be used consists of a gravimetric feeder for the raw materials, a twin-screw extruder for the slurry crystallisation reaction, followed by a fluidised bed dryer, or a vacuum microwave dryer, and a granulator.

The raw materials for the method are hydrogen peroxide, in the form of an aqueous solution concentrated from 30 to 80%, and a salt of citric acid. The citric acid salt may, inter alia, be obtained by partial or total neutralisation of the citric acid with a carbonate, a hydroxide or one of its own salts, the cations of which are selected from the alkali, alkaline earth, transition or post-transition metals suitable for the production of the desired citrate perhydrate of the present invention. The citric acid may, inter alia, be neutralised prior to the crystallisation reaction by mixing the powders or directly within the extruder by individually injecting each component.

Step 1: Crystallisation Reaction

The raw materials are injected into a twin-screw extruder using a gravimetric feeder. The quantity of raw materials injected observes the stoichiometry of the desired citrate perhydrate of the present invention. For example, in the case of the preparation of anhydrous disodium citrate monoperhydrate, one possible production method is the crystallisation of 2 mol of trisodium citrate and 1 mol of citric acid with 3 mol of hydrogen peroxide.

The raw materials are mixed within the twin-screw extruder and begin to crystallise at controlled temperature and residence time, to produce a solid at the outlet of the extruder. For example, in the case of the production of an anhydrous disodium citrate monoperhydrate, the crystallisation temperature is 55-65° C. and the residence time is approximately 1 minute, when the solid raw materials used are anhydrous. It should be noted that the use of hydrated solid raw materials requires an extruder fitted with a degassing system, greatly reduces the exothermic nature of the reaction and can significantly prolong the residence time in the extruder.

At this stage, the solid obtained at the outlet of the extruder is thixotropic and can be readily shaped, for instance into granules, without agglomerating.

In order to complete the crystallisation of the desired citrate perhydrate of the present invention, the solid obtained at the outlet of the extruder is cooled down to 15-25° C. by natural convection. The discharging of excess water from the crystallisation reaction can be observed visually on the surface of the solid.

Step 2: Drying and Grinding

Once crystallised, the citrate perhydrate can be dried at a controlled temperature using a fluidised bed dryer or a vacuum microwave dryer, then ground to the desired particle size, since, at this final stage, the product is no longer thixotropic. For example, in the case of the production of an anhydrous disodium citrate monoperhydrate, the drying temperature is 40-60° C.

Variant for Production of a Citrate Perhydrate Co-Crystallised with Urea Perhydrate.

A citrate perhydrate according to the present invention can be produced by co-crystallisation with urea to form a co-crystal of citrate perhydrate and urea perhydrate.

To this end, urea is also injected by gravimetric feeding into the twin-screw extruder. The molar ratios to be observed range from 1 to 5 mol of urea per mole of salt of citric acid, preferentially 3 mol of urea per mole of salt of citric acid.

The amount of hydrogen peroxide should be adapted to observe the stoichiometry of the desired crystals of citrate perhydrate resulting from the present invention and of urea perhydrate. For example, in the case of producing a co-crystallisation of 1 mol of trisodium citrate monoperhydrate dihydrate and 3 mol of urea perhydrate, 4 mol of hydrogen peroxide crystallise with 1 mol of trisodium citrate and 3 mol of urea.

This production method has significant advantages over independent production of urea perhydrate which is then mixed in solid form with the citrate perhydrates produced.

This is because the urea perhydrate available on the European market is sold at approximately 20 €/kg while urea is sold at less than 1 €/kg. Moreover, urea perhydrate produced independently is generally stabilised by adding stabiliser which is relatively toxic, which does not make it compatible with a zero-residue biobased biocide such as the citrate perhydrates of the present invention, whereas urea perhydrate produced by co-crystallisation with a citrate perhydrate is stable without adding stabilisers. This is probably due to the presence of citrate as a natural and non-toxic stabiliser.

Variant for Production of a Citrate Perhydrate from an Alcohol-Based Solution.

A citrate perhydrate can be obtained by crystallisation in an alcohol-based solution.

To this end, a first solution is prepared containing the salt of citric acid and hydrogen peroxide, the amounts of which observe the stoichiometry of the desired citrate perhydrate resulting from the present invention. The citric acid salt may, inter alia, be obtained by partial or total neutralisation of the citric acid with a carbonate, a hydroxide or one of its own salts, the cations of which are selected from the alkali, alkaline earth, transition or post-transition metals suitable for the production of the desired citrate perhydrate resulting from the present invention.

A second solution is prepared: an alcohol-based solution, in which the alcohol contains in particular from 1 to 5 carbon atoms and which may more particularly be ethanol. This solution may also be the alcohol itself.

These two solutions are subsequently mixed. The volume ratio of the alcohol-based solution is between 3.7:1 and 8:1 relative to the first aqueous solution containing the citrate and the hydrogen peroxide.

The citrate perhydrates produced precipitate in the form of crystals and are recovered using liquid-solid separation techniques known to the person skilled in the art (filtration, centrifugation, etc.) and are optionally dried at 40-60° C.

Example 2: Trisodium Citrate Monoperhydrate Dihydrate

The trisodium citrate monoperhydrate dihydrate was prepared as indicated in example 1.

2.1. Crystalline Structure
Materials and Methods
Powder X-Ray Diffraction

The samples were carefully ground to a fine powder using a pestle and mortar. The powder X-ray diffraction data was collected using a PANalytical XPERT-PRO diffractometer (Bragg-Brentano geometry, Cu Kα radiation (λ=1.5418 Å), generator settings: 45 kV and 30 mA). The powder graphs were measured from 4 to 40°, 2θ, and the measurement time was from 6 to 15 minutes.

Results

The diffractogram obtained, given in FIG. 2, and also the characteristic lines in table 1, show an unknown crystalline structure which differs from the starting product, from trisodium citrate, and from all its hydrated forms:

TABLE 1

Characteristic lines of trisodium citrate monoperhydrate dihydrate

| Peaks | 2θ | Relative intensity | hkl index |
|---|---|---|---|
| 1 | 9.924509 | 100 | 0 0 1 |
| 2 | 8.740994 | 5.95 | 0 1 0 and 0 1 -1 |

TABLE 1-continued

Characteristic lines of trisodium citrate monoperhydrate dihydrate

| Peaks | 2θ | Relative intensity | hkl index |
|---|---|---|---|
| 3 | 6.148828 | 0.87 | 1 0 0 |
| 4 | 5.519614 | 15.76 | −1 0 1 |
| 5 | 5.483783 | 36.95 | 0 −1 2 |
| 6 | 5.372527 | 51.54 | −1 1 0 |
| 7 | 4.959513 | 16.42 | −1 −1 1 and 0 0 2 |
| 8 | 4.871902 | 5.55 | 0 −2 1 |
| 9 | 4.740059 | 4.39 | 1 1 0 |
| 10 | 4.413263 | 36.26 | −1 1 1 |
| 11 | 4.381867 | 6.14 | 0 −2 2 |
| 12 | 4.364081 | 19.23 | 0 2 0 |
| 13 | 4.094722 | 2.37 | −1 0 2 |
| 14 | 4.000887 | 38.77 | 1 −2 1 and 1 −1 2 |
| 15 | 3.679708 | 4.92 | 0 −1 3 |
| 16 | 3.660295 | 10.8 | 1 0 2 and −1 −2 1 |
| 17 | 3.62327 | 22.99 | 1 −2 2 |
| 18 | 3.514807 | 11.02 | −1 −2 2 |
| 19 | 3.483591 | 3.3 | 0 −2 3 |
| 20 | 3.466081 | 14.3 | 0 2 1 |

The characteristics of the crystal of trisodium citrate monoperhydrate dihydrate are given in table 2 below:

TABLE 2

Characteristics of the crystalline structure of trisodium citrate monoperhydrate dihydrate

| | | |
|---|---|---|
| Chemical formula | | C6 H11 O11 Na3 |
| Molecular weight | | 328.12 g/mol |
| Sodium citrate | % by weight | 78.7 |
| | molar ratio | 1 |
| Hydrogen peroxide | % by weight | 10.4 |
| | molar ratio | 1 |
| Water | % by weight | 10.9 |
| | molar ratio | 2 |
| Space group | | P-1 |
| Crystal system | | Triclinic |
| Length of unit cell (a) | | 6.2400 (4) Å |
| Length of unit cell (b) | | 9.8204 (5) Å |
| Length of unit cell (c) | | 11.1233 (7) Å |
| α | | 115.846 (6) Å |
| β | | 93.600 (5) Å |
| γ | | 95.350 (5) Å |
| Unit cell volume | | 606.69 (7) Å. |
| ρ calculated | | 1.796 cm$^3$ |

The asymmetric unit contains an entirely deprotonated citrate anion, three sodium cations, two water molecules and two half molecules of hydrogen peroxide. Thus, the chemical formula given is $Na_3C_6H_{11}O_{11}$, as presented below and in FIG. 3.

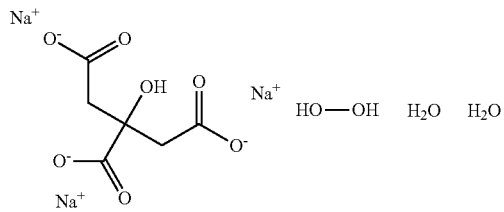

Molecular structure of trisodium citrate monoperhydrate dihydrate 2.2 Water-Solubility The solubility of the compounds of the invention is determined by experiments at increasing concentrations of the compound of the invention in deionised water. The results show that trisodium citrate monoperhydrate dihydrate is entirely water soluble (>900 g/l at 20° C.).

2.3 pH of an Aqueous Solution of the Compound

The pH measurements (using a pH meter) show that an aqueous solution of trisodium citrate monoperhydrate dihydrate diluted 20× is 7.6 (±0.3).

Example 3: Anhydrous Disodium Citrate Monoperhydrate

The anhydrous disodium citrate monoperhydrate was prepared as indicated in example 1.

3.1. Crystalline Structure

The powder X-ray diffraction data was collected using a Cu Kα diffractometer as described above and supplemented by synchrotron radiation measurements.

The diffractogram obtained, presented in FIG. 4, and its characteristic lines given in table 3, show a crystalline structure unknown from databases, which differs from citric acid, from trisodium citrate and all its hydrated forms, from disodium citrate and all its hydrated forms, and also from trisodium citrate perhydrate.

TABLE 3

Characteristic lines of anhydrous disodium citrate monoperhydrate

| Peaks | 2θ | Relative intensity | hkl index |
|---|---|---|---|
| 1 | 7.10442 | 2.42 | 0 1 1 |
| 2 | 6.53808 | 6.93 | 1 1 1 |
| 3 | 6.19763 | 11.5 | 0 2 0 |
| 4 | 5.03008 | 18.94 | 2 2 0 |
| 5 | 4.83206 | 0.76 | 1 2 1 |
| 6 | 4.45527 | 10.07 | 3 1 1 |
| 7 | 4.34762 | 32.9 | 2 2 1 |
| 8 | 4.29193 | 11.19 | 4 0 0 |
| 9 | 4.21333 | 17.21 | 3 2 0 |
| 10 | 3.97003 | 19.47 | 1 1 2 |
| 11 | 3.85293 | 13.47 | 4 0 1 and 2 0 2 |
| 12 | 3.78756 | 19.04 | 3 2 1 |
| 13 | 3.67804 | 12.75 | 4 1 1 |
| 14 | 3.53769 | 100 | 4 2 0 |
| 15 | 3.47303 | 5.61 | 1 2 2 |
| 16 | 3.42705 | 7.44 | 2 3 1 |
| 17 | 3.32368 | 6.66 | 3 1 2 |
| 18 | 3.2801 | 32.86 | 2 2 2 |
| 19 | 3.13095 | 31.11 | 3 3 1 |
| 20 | 3.09689 | 19.5 | 5 1 1 |

The characteristics unique to the crystal of disodium citrate perhydrate are given in table 4.

TABLE 4

Characteristics of the crystalline structure of anhydrous disodium citrate monoperhydrate

| Crystal system | Orthorhombic #61 Pbca |
|---|---|
| Length of unit cell (a) | 8.6396 (25) Å |
| Length of unit cell (b) | 12.433 (4) Å |
| Length of unit cell (c) | 17.199 (5) Å |
| Unit cell volume | 1847.5 (8) Å³ |

The measurements regarding the H bonds are given in table 5 below:

TABLE 5

Hydrogen bonds in the crystalline structure of anhydrous disodium citrate monoperhydrate (*intramolecular)

| H bond | D-A, Å | H···A, Å | D···A, Å | D-H···A, Å | Overlap, e | E, kcal/m |
|---|---|---|---|---|---|---|
| O12-H21···O13 | 1.041 | 1.507 | 2.546 | 175.0 | 0.092 | 16.6 |
| O17-H18···O22 | 0.976 | 1.852 | 2.770 | 155.7 | 0.041 | 11.1 |
| O17-H18···O13 | 0.976 | 2.557* | 3.063 | 112.5 | 0.009 | 5.2 |
| O22-H24···O13 | 1.015 | 1.585 | 2.598 | 174.7 | 0.080 | 15.5 |
| O23-H25···O13 | 0.994 | 1.605 | 2.596 | 174.8 | 0.064 | 13.8 |
| C4-H10···O13 | 1.094 | 2.340 | 3.270 | 141.8 | 0.015 | |
| C2-H7···O13 | 1.095 | 2.482* | 3.199 | 121.9 | 0.012 | |

The asymmetric unit corresponds to the formula $Na_2HC_6H_5O_7(H_2O_2)$, and thus contains a citrate anion, two sodium cations and a molecule of hydrogen peroxide as presented below. There are no spaces in the structure to accommodate a water molecule.

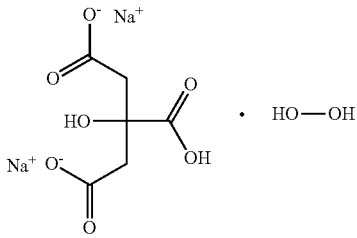

3.2. Water-Solubility

The disodium citrate perhydrate is entirely water soluble (>800 g/l at 20° C.).

3.3. pH of an Aqueous Solution of the Compound

The pH measurements (using a pH meter) show that, diluted (20×) in water, the disodium citrate perhydrate crystals obtained have a pH of 5.2 (±0.3).

3.4. Thermogravimetric Analysis (TGA)

Thermogravimetric analyses of a crystalline powder of disodium citrate perhydrate according to example 1 were carried out, to assess the behaviour thereof at a temperature of from 100 to 220° C.

The TGA mass loss graphs were obtained with a TA instruments (Waters) instrument under a nitrogen atmosphere and in the temperature range of between 30 and 250° C. A temperature ramp of 10° C./min was set up, followed by a hold at the final temperature (250° C. for this analysis) for a period of 10 minutes.

A mass loss of less than 1% takes place below 140° C., probably corresponding to loss of water of crystallisation. The powder then lost between 2 and 3% of its mass between 140 and 220° C.

These results demonstrate excellent stability at high temperatures.

Example 4: Co-Crystallisation of One Mole of Anhydrous Disodium Citrate Monoperhydrate and 3 Mol of Urea Perhydrate 4.1. Crystalline Structure The diffractogram obtained is presented in FIG. 5.

The diffraction spectrum obtained shows that the powder produced is a co-crystallisation of anhydrous disodium citrate monoperhydrate and urea perhydrate, the most characteristic peaks of which are highlighted.

4.2 pH of an Aqueous Solution of the Compound

The pH of an aqueous solution of the co-crystals of one mole of anhydrous disodium citrate monoperhydrate and 3 mol of urea perhydrate, diluted 20×, is 5.2 (±0.3).

Example 5: Performance

1. Formulation 1 Based on Co-Crystallised Trisodium Citrate Monoperhydrate Dihydrate and Urea Perhydrate 1.1. Preparation of the Formulation 200 g of a co-crystallisation containing 1 mol of trisodium citrate monoperhydrate dihydrate and 4 mol of urea perhydrate are mixed with 21 g of urea and 55 g of anhydrous citric acid. The mixture of powders is then dissolved in deionised water at different concentrations.

1.2. Biocidal Performance in Biotests

Formulation 1 is tested in biotests on various pathogens. The results are presented in table 6.

TABLE 6

| Effective concentration [mg/ml] of formulation 1. | |
|---|---|
| Plasmopara viticola | 24 |
| Botiytis cinerea | <5 |
| Guignardia bidwellii | 5 |
| Helminthosporium solani | 25 |
| Collelotrichum coccodes | 25 |
| Monilia laxa strain 623 | 18 |
| Monilia laxa INRA strain | 50 |
| Serpula lacrimens | 18 |
| Staphylococcus aureus | 0.064 |
| Pseudomonas aeruginosa | 0.256 |
| Erwinia amylovora | 1.024 |
| Ralstonia strain 06 | 0.512 |
| Ralstonia strain R1 | 0.512 |

2. Formulation 2 Based on Anhydrous Disodium Citrate Monoperhydrate 2.1. Preparation of the Formulation The powder of example 3 is dissolved in deionised water at different concentrations.

2.2. Antifungal Performance

Formulation 2 is tested in biotests on various pathogens. The results are presented in table 7.

TABLE 7

| Effective concentration [mg/ml] of formulation 2. | |
|---|---|
| Erysiphe necator | 10 |
| Botrytis cinerea | 5-10 |
| Monilia laxa strain 623 | 10-20 |

TABLE 7-continued

| Effective concentration [mg/ml] of formulation 2. | |
|---|---|
| Monilia laxa INRA strain | 34-50 |
| Monilia fructigena | 34-50 |

3. Formulation 3 Based on Co-Crystallised Anhydrous Disodium Citrate Monoperhydrate and Urea Perhydrate 3.1 Preparation of the Formulation The powder of example 4 is dissolved in deionised water at different concentrations.

3.2. Antifungal Performance

Formulation 3 is tested in biotests on the fungi *Plasmopara viticola, Erysiphe necator, Guignardia bidwellii* and *Monilia fructigena*. The results are presented in table 8.

TABLE 8

| Effective concentration [mg/ml] of formulation 3 | |
|---|---|
| Plasmopara viticola | 30 |
| Erysiphe necator | 10 |
| Botrytis cinerea | 1-5 |
| Guignardia bidwellii | 25-50 |
| Monilia laxa strain 623 | 10-20 |
| Monilia laxa INRA strain | 17-25 |
| Monilia fructigena | 17-25 |

4. Formulation 4 Based on Co-Crystallised Anhydrous Disodium Citrate Monoperhydrate and Urea Perhydrate 4.1. Preparation of the Formulation 62 g of the powder described in example 4 are mixed with 10 g of anhydrous citric acid, 3 g of lactic acid, 2 g of anhydrous calcium lactate, 1.5 g of a surfactant and 1.5 g of a desiccant. The powder mixture is then dissolved in deionised water at different concentrations.

4.2. Antibacterial Performance

Formulation 4 is tested in biotests on six pathogenic strains according to standard EN1040. The results are presented in FIG. 6.

5. In Vitro Tests

The efficacy of formulations 2 and 3 as described above is analysed using biotests on the fungus *Botritys cinerea* in terms of conidia germination (table 9) and mycelium growth (table 10) compared with the reference chemical fungicide (Teldor, Bayer), as well as biotests on the fungus *Venturia inaequalis* in terms of conidia germination (table 11) compared with the reference chemical fungicide (Merpan, Adam France).

TABLE 9 efficacy (%) of formulations 2 and 3 in relation to *Botritys cinerea (conidia germination)*

| | formulation/concentration (mg/ml) | | |
|---|---|---|---|
| | 2 | 5 | 10 |
| Formulation 2 | — | 100 | 100 |
| Formulation 3 | 100 | 100 | 100 |
| Teldor (reference) | 79 | 81 | 81 |

TABLE 10 efficacy (%) of formulations 2 and 3 in relation to
*Botritys cinerea* (mycelium growth)

| | formulation/concentration (mg/ml) | | | | |
|---|---|---|---|---|---|
| | 5 | 10 | 15 | 20 | 30 |
| Formulation 2 | 25-49.99 | 50-74.999 | 50-74.999 | 50-74.999 | 75-100 |
| Formulation 3 | 75-100 | 75-100 | 75-100 | 75-100 | 75-100 |
| Teldor (reference) | 50-74.999 | 50-74.999 | 50-74.999 | 50-74.999 | — |

TABLE 11 efficacy (%) of formulations 2 and 3 in relation to
the fungus *Venturia inaequalis* (conidia germination)

| | Formulation/concentration (mg/ml) | | |
|---|---|---|---|
| | 2 | 5 | 10 |
| Formulation 2 | 100 | 100 | 100 |
| Formulation 3 | 100 | 100 | 100 |
| Merpan (reference) | 100 | 100 | 100 |

6. Antifungal Performance: Other Field Validation

The experiment is performed on a Swiss vineyard in accordance with good agricultural practices (GAP) as defined in Article R 253-1 of the French Rural Code for data relating to the biological evaluation of plant-protection products. The test aims to evaluate the growth of powdery mildew both on leaves and bunches of grapes. Seedlings are treated weekly by application of a spray mixture at 200 l/ha. The test plots are described as indicated below:

An untreated plot (TNT);
A plot treated with formulation 3 at 30 g/l, to which 1% $SiO_2$ and 0.5% heptamethyltrisiloxanes (wetting agent, De Sangosse—Agridyne) have been added, corresponding to 6 kg per hectare of vines (Biogel solo);
A plot treated which a customary reference chemical fungicide (customary schedule);
A plot treated with a reference fungicide authorised for organic agriculture (organic schedule).

The efficacy of the formulation tested is evaluated based on 2 criteria: the percentage incidence and severity of the disease, both on the leaves (FIG. 8A) and on the grapes (FIG. 8B).

Example 6: Instability of Concentrated Solutions of Citric Acid and Hydrogen Peroxide The stability of a concentrated solution of hydrogen peroxide and citric acid is studied.

To this end, a solution containing 37.5% hydrogen peroxide and 25% citric acid is prepared. The concentration of hydrogen peroxide is then measured using permanganate titration three times over two months. The content of per-acids is also measured based on a colorimetric test strip method.

The results are presented in table 12:

TABLE 12

Results of the change in a solution containing
37.5% hydrogen peroxide and 25% citric acid

| Date of measurements | wt % Hydrogen peroxide | wt % Peracids |
|---|---|---|
| D 0 | 37.5 | 0 |
| D 0 + 16 days | 32.6 | 5 |
| D 0 + 2 months | 24.6 | 5 |

These results show that the solution loses 34.4% of its concentration in hydrogen peroxide after 2 months. 5% peracids are also observed to appear in solution after 18 days. Moreover, an increase in pressure followed by gas release is observed over time.

Example 7: Comparative Performance of the Citrate Perhydrates of the Invention Compared to Aqueous Solutions of Hydrogen Peroxide, Citrates and Citric Acid 1. Action on *Botrytis cinerea*

Tests carried out according to a standard protocol on different target fungi, including *Botrytis cinerea*, showed that, at equivalent concentrations, neither the citrate alone nor the hydrogen peroxide alone have a fungicidal or fungistatic effect, unlike the compounds of the invention (cf. table 13 below).

This is moreover confirmed by Gil-ad et al. (*FEMS Microbiology Letters* 1999, 176, 455-461), indicating that *Botrytis cinerea* can germinate in the presence of hydrogen peroxide at concentrations up to 180 mM (6 mg/ml), and its mycelium can grow at even higher concentrations.

TABLE 13

Comparative results of biotests on *Botrytis cinerea* (Agroscope 07-2019)

| Échantillon | Formule chimique | pH | $H_2O_2$ (M) | Citrate (M) | Na/Citrate | MIC Botrytis (mM) |
|---|---|---|---|---|---|---|
| Disodium citrate sesquihydrate | $Na_2 H C_6H_5O_7 1 ½H_2)O$ | 4.9 | 0 | 0.2 | 2 | non actif |
| Disodium citrate perhydrate | $Na_2 H C_6H_5O_7 H_2O_2$ | 4.9 | 0.2 | 0.2 | 2 | 108 |
| Trisodium citrate perhydrate | $Na_3 C_6H_5O_7 H_2O_2 2 H_2O$ | 8.2 | 0.2 | 0.2 | 3 | 72 |
| Hydrogen peroxide | $H_2O_2$ | 6.4 | 0.2 | 0 | 0 | non actif |
| Acide citrique | $C_6H_8O_7$ | | | | | non actif |

[Key:
échantillon = sample;
Formule chimique = Chemical formula;
Acide citrique-Citric acid;
non actif-not active]

The disodium citrate perhydrate preferably crystallises with the hydrogen peroxide, rather than with the water, and forms a reactive biocidal barrier. Indeed, when the disodium citrate perhydrate is placed in aqueous solution for spraying, i.e. when the disodium citrate and the hydrogen peroxide are sprayed onto a surface, the water evaporates and the disodium citrate perhydrate evaporates again to form a reactive biocidal barrier, whereas a solution of hydrogen peroxide simply evaporates. This enables a persistent effect for the product of the invention.

2. Action on *Staphylococcus aureus*

Tests were carried out according to a standard protocol on *Staphylococcus aureus* MRSA, comparing the disodium citrate perhydrate of the invention to sodium citrate, to hydrogen peroxide and to a reference antiseptic.

The results of these tests are given in table 14:

TABLE 14

Comparative results of biotests on *Staphylococcus Aureus* MRSA

| | MIC value | % | mM |
|---|---|---|---|
| Sodium citrate (pH 5 -> 8) | 3.20 mg/ml | 0.320 | 12.40 -> 13.56 |
| Hydrogen peroxide | 0.94 mg/ml | 0.094 | 27.58 |
| PVP-I (Povidone-iodine) | 6.25 mg/ml | 0.625 | 17.13 |
| Ethanol | 87.5 mg/ml | 8.750 | 1899.35 |
| Disodium citrate per hydrate of the invention | 0.03 mg/ml | 0.003 | 0.12 |

Given the molecular structure of the disodium citrate perhydrate, the comparison of the efficacy of the compound of the invention compared to sodium citrate and hydrogen peroxide is easy (in equimolar amounts).

It should be noted that the disodium citrate perhydrate has a growth-inhibiting efficacy (MIC) for *Staphylococcus aureus* MRSA which is 230 times greater than that of hydrogen peroxide alone and 103 times greater than sodium citrate.

The invention claimed is:

1. A citrate perhydrate of alkali metal being a disodium citrate perhydrate, wherein the disodium citrate perhydrate is in a powder form, the powder being physically and chemically stable without significant alteration after one year at a temperature of from 20 to 25° C., in their physical state and in their chemical composition with regard to the concentration of active oxygen.

2. The citrate perhydrate of alkali metal according to claim 1, being an anhydrous disodium citrate monoperhydrate.

3. The citrate perhydrate of alkali metal according to claim 1, having a solubility greater than or equal to 850 g/l at 25° C. in water.

4. The citrate perhydrate of alkali metal according to claim 1, having a pH in aqueous solution of 5.2.

5. The citrate perhydrate of alkali metal according to claim 1 that when subjected to a temperature ranging from 100° C. and 220° C., measured by thermogravimetric analysis under a nitrogen atmosphere and in the temperature range of between 30 and 250° C. following a temperature ramp of 10° C./min, followed by a hold at the final temperature for a period of 10 minutes such that the powder shows a mass loss of less than 1% below 140° C., and between 2 and 3% between 140 and 220° C.

6. The citrate perhydrate of alkali metal according to claim 1, in the form of a crystal formed of disodium citrate and hydrogen peroxide.

7. A composition comprising the citrate perhydrate as defined in claim 1, and urea perhydrate in the form of a urea-hydrogen peroxide co-crystal.

8. An antimicrobial agent for use in humans or animals, comprising disodium citrate perhydrate according to claim 1.

9. A tooth whitening agent for a use in dental medicine comprising disodium citrate perhydrate according to claim 1.

10. A pharmaceutical composition or phytopharmaceutical composition constituted by or comprising a disodium citrate perhydrate according to claim 1.

11. A biocide composition comprising a disodium citrate perhydrate according to claim 1.

12. The biocide composition according to claim 11, wherein the disodium citrate perhydrate is in the form of a crystal formed of disodium citrate and hydrogen peroxide.

13. The biocide composition according to claim 11, further comprising water and/or at least one additional compound selected from pH regulators, anti-agglomerating agents, surfactants, wetting agents, antifoaming agents, anti-drift agents, thickeners, foaming agents, solidifying agents, fertilizers, phytopharmaceutical products, stabilisers, glycolipids and mixtures thereof.

14. A method for inhibiting or preventing the growth of a pathogen on or in a plant, wherein said disodium citrate perhydrate according to claim 1 is applied to the surface of the plant in an amount of from 25 to 1000 ng·dm$^{-2}$.

15. The method for inhibiting or preventing the growth of a pathogen on or in a plant according to claim 14, wherein said disodium citrate perhydrate is applied in the presence of water and/or at least one additional compound selected from pH regulators, anti-agglomerating agents, surfactants, wetting agents, antifoaming agents, anti-drift agents, thickeners, foaming agents, solidifying agents, fertilizers, phytopharmaceutical products, stabilisers, glycolipids and mixtures thereof.

16. The method for inhibiting or preventing the growth of a pathogen on or in a plant according to claim 14, wherein said disodium citrate perhydrate is applied in the presence of urea perhydrate in the form of urea-hydrogen peroxide co-crystals.

17. The method for inhibiting or preventing the growth of a pathogen on or in a plant according to claim 14, wherein the pathogen is selected from viruses, bacteria, fungi and pseudofungi, and wherein the plant is selected from fruit-bearing plants, vegetable-bearing plants, ornamental plants, turf and cereals.

18. A method for disinfecting a fluid or a surface, comprising applying disodium citrate perhydrate according to claim 1 to the fluid or to the surface.

19. The method for disinfecting a fluid or a surface according to claim 18, wherein said disodium citrate perhydrate is co-crystallised with urea perhydrate in the form of urea-hydrogen peroxide co-crystals.

20. A method for preparing a citrate perhydrate of alkali metal according to claim 1, said method comprising:
(i) a step of bringing a disodium citrate into contact with hydrogen peroxide, to obtain said disodium citrate perhydrate,
said step (i) optionally being preceded by a step of neutralisation of a citric acid with a hydroxide, a carbonate or a citrate of sodium, in order to obtain the disodium citrate as mentioned in step (i), or (i') a step of bringing into contact citric acid; a hydroxide, carbonate or citrate of sodium; and hydrogen peroxide, to obtain said disodium citrate perhydrate of alkali, alkaline earth, transition or post-transition metal.

21. A method for preparing a composition according to claim 7, said method comprising a step (a) of co-crystallisation by bringing into contact a disodium citrate, urea, and hydrogen peroxide, said step (a) optionally being preceded by a step of neutralisation of a citric acid with a hydroxide, a carbonate or a citrate of sodium, in order to obtain the disodium citrate as mentioned in step (a), or (a') a step of bringing into contact citric acid; a hydroxide, carbonate or citrate of sodium; urea; and hydrogen peroxide, to obtain said disodium citrate perhydrate.

* * * * *